United States Patent
Evans et al.

[11] Patent Number: 5,958,911
[45] Date of Patent: Sep. 28, 1999

[54] METHOD OF RELIEVING INFLAMMATION BY USING 5-ALKYLSULFONYLSALICYLANILIDES

[75] Inventors: Richard T. Evans, E. Amherst; Robert A. Coburn, Williamsville; Robert A. Genco, Bufffalo; Joseph A. Dunn, Amherst, all of N.Y.

[73] Assignees: The Research Foundation of State University of New York; Therex Technologies, Inc., both of Amherst, N.Y.

[21] Appl. No.: 08/963,751

[22] Filed: Nov. 4, 1997

Related U.S. Application Data

[60] Provisional application No. 60/030,303, Nov. 5, 1996.

[51] Int. Cl.⁶ .................................................. A61K 31/615
[52] U.S. Cl. ............................................................ 514/166
[58] Field of Search ............................................. 514/161

[56] References Cited

U.S. PATENT DOCUMENTS

| | | | |
|---|---|---|---|
| 4,287,191 | 9/1981 | Coburn et al. | 424/230 |
| 4,358,443 | 11/1982 | Coburn et al. | 514/166 |
| 4,742,083 | 5/1988 | Ritchey | 514/617 |
| 4,939,132 | 7/1990 | Coburn et al. | 514/166 |
| 5,240,696 | 8/1993 | Van Der Ouderaa et al. | 424/49 |

OTHER PUBLICATIONS

Clark et al., J. Med. Chem., 29(1) pp. 25–29.

*Primary Examiner*—Phyllis G. Spivack
*Attorney, Agent, or Firm*—Hodgson, Russ, Andrews, Woods & Goodyear, LLP

[57] ABSTRACT

A method of treating inflammation in a mammal, which comprises contacting the affected area with an amount sufficient to ameliorate the inflammatory condition, of a compound of the following formula

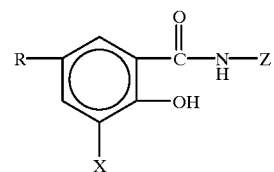

in a pharmaceutically acceptable carrier containing a detergent, where Z is a substituted phenyl, R is a substituted or unsubstituted alkylsulfonyl group from 1 to 20 carbon atoms and X is —CN, —NO$_2$, —H, halogen, lower alkyl or lower haloalkyl radical.

33 Claims, No Drawings

METHOD OF RELIEVING INFLAMMATION BY USING 5-ALKYLSULFONYLSALICYLANILIDES

This Application claims the priority of a U.S. Provisional Patent Application, serial No. 60/030,303 entitled "Method of Relieving Inflammation by Using 5-alkylsulfonylsalicylanilides" filed on Nov. 5, 1996.

This invention was made with government support under grant 1R41DE11618A awarded by the National Institutes of Health. The government has certain rights in the invention.

FIELD OF THE INVENTION

The present invention relates to a novel method for the relief of inflammation of tissues affected by disease such as periodontal disease. More particularly, the present invention provides a method for the topical application of lipophilic salicylanilide derivatives that have minimal systemic absorption and are easily solubilized in aqueous solutions containing ionic or nonionic detergents.

BACKGROUND OF THE INVENTION

Bacterial infections are often accompanied by inflammation of the infected tissues. For example, during pathogenesis of periodontal disease, it is generally accepted that while bacteria cause tissue destruction via release of virulence factors, a major role has been proposed for the host itself. The current concept is that bacteria produce inflammogens including lipopolysaccharides, which trigger mononuclear host cells resulting in bone and connective tissue destruction. These destructive mechanisms include periodontal triggering of macrophage and fibroblast collagenase which degrades tissue collagen, and stimulation of the production, by mononuclear cells, of interleukin-2 and other cytokines which stimulate local bone resorption.

While antibiotics have been successfully used to treat periodontitis, recent studies show that anti-inflammatory agents also reduce chronic destructive periodontitis (Williams et al. 1989, *J. Periodontology* 60:485–490; Reddy et al. 1993, *J. Clinical Periodontology* 20:635–640). Most of the anti-inflammatory approaches used so far utilize the systemic non-steroidal anti-inflammatory flurboprofen which has a risk of adverse systemic effects such as gastric ulcers. Furthermore, most anti-inflammatory agents that have been proposed for topical application are designed for systemic use and hence have significant systemic absorption potential, especially when used over long periods of time.

One group of anti-inflammatory compounds disclosed previously includes salicylanilides. U.S. Pat. No. 4,742,083 (Ritchey) discloses anti-inflammatory uses of substituted salicylanilides of the general formula:

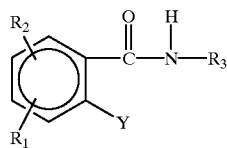

wherein $R_1$, $R_2$ and $R_3$ are defined hydrocarbon attachments and Y is —OH or a phenolic ester group. These salicylanilide derivatives have also been shown to be effective anti-plaque agents (Coburn et al. U.S. Pat. Nos. 4,287,191; 4,358,443). The most effective of these compounds is defined by the formula:

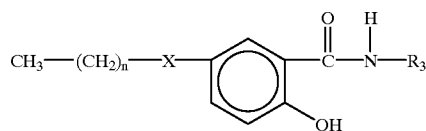

where n=6, X is

and —$R_3$ is a meta-trifluoromethylphenyl group (AMCF3-8 in U.S. Pat. No. 4,742,083). This compound has a pKa of 6.1 rendering it relatively insoluble in aqueous solutions at neutral pH.

Another anti-inflammatory compound disclosed previously for both systemic and topical use is 2',4,4'-trichloro-2-hydroxy-diphenyl-ether, also known as Triclosan™ (Van Der Ouderaa et al. U.S. Pat. No. 5,240,696).

Thus, currently available topical anti-inflammatory compounds have either high systemic absorption or low solubility in formulations typically used in topical applications. A need therefore exists for effective anti-inflammatory compounds that are lipophilic thereby reducing the risk of systemic absorption, and are also easily solubilized in formulations suitable for topical application.

SUMMARY OF THE INVENTION

An object of the present invention is to provide methods for relief of topical inflammation in mammals.

Another object of the present invention is to provide methods for the use of lipophilic agents that are minimally absorbed systemically, are effective against inflammation and can be incorporated into suitable topical formulations.

A yet another object of the present invention is to provide methods for the topical use of 5-alkylsulfonylsalicylanilide derivatives in the management of inflammation.

A still further objective of the present invention is to provide methods for the use of 5-alkylsulfonylsalicylanilide derivatives in the management of inflammation of tissues in periodontal disease.

DESCRIPTION OF THE INVENTION

The present invention is concerned with certain 5-alkylsulfonyl derivatives of salicylanilides. These compounds have previously been shown to have antimicrobial properties especially against the microorganisms associated with dental plaques and associated oral diseases.

The method of the present invention involves the use of compounds encompassed by the following formula:

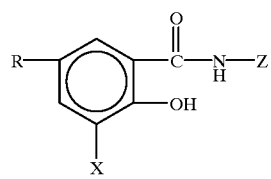

wherein Z is a substituted phenyl ring from 6 to 30 carbon atoms including substituents; R is a substituted or unsubstituted alkylsulfonyl group of from 1 to 20 carbon atoms including substituents; and, X is a radical selected from the group consisting of —CN, —NO$_2$, —H, halogen, lower alkyl or lower haloalkyl.

"Lower alkyl" as used herein means an alkyl group of from 1 to 10 carbon atoms.

In the preferred compounds of this invention, R is substituted or unsubstituted alkylsulfonyl group of from 6 to 14 carbons, the substituted moiety in the phenyl ring of the Z group has an electron withdrawing effect on the phenyl ring, and the partition coefficient is greater than 4.

"Partition coefficient" as used herein is the log$_{10}$ P where P is the ratio of the molar concentrations of the composition in octanol-water system. Partition coefficient is a measure of the lipophilic character of the compound. A partition coefficient of 4 therefore means that the ratio of the concentration of the composition in octanol to the concentration in water is 10$^4$ or 10,000 to 1.

"High lipophilicity" as used herein means a partition coefficient of greater than 4.

"Substituted" as used herein means that at least one hydrogen in the compound is replaced with a moiety containing one or more carbon, oxygen, sulfur, nitrogen or halogen atoms.

A generic formula which includes many compounds of the present invention is:

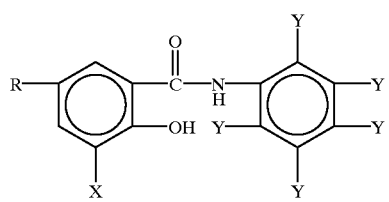

where R is an alkylsulfonyl group containing 1 to about 20 carbon atoms; X is as previously described; and Y is an electron withdrawing group and desirably is not strongly hydrophilic or water solubilizing. Some good Y groups are —CF$_3$, —CN and —NO2. In a preferred embodiment, X is —H, and Y is —CF$_3$ or —CN attached at the meta or para position.

Some examples of specific compounds in accordance with the invention have the formula:

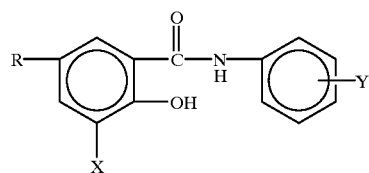

where R is

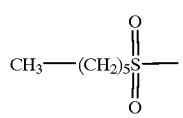

X is —H and Y is —CF$_3$ (TMF-6), or —CN (TMC-6) attached at the meta position;

where R is

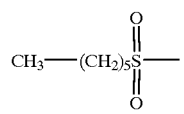

X is —H and Y is —CN (TPC-6) at the para position;
where R is

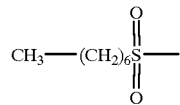

X is —H and Y is —CF$_3$ (TMF-7), or —CN (TMC-7) attached at the meta position;
where R is

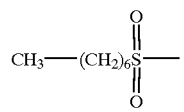

X is —H and Y is —CN (TPC-7) attached at the para position;
where R is

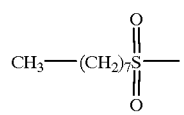

X is —H and Y is —CF$_3$ (TMF-8), or —CN (TMC-8) attached at the meta position;
where R is

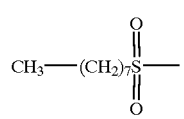

X is —H and Y is —CN (TPC-8) attached at the para position;
where R is

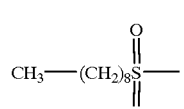

X is —H and Y is —CF$_3$ (TMF-9), or —CN (TMC-9) attached at the meta position;
where R is

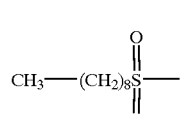

X is —H and Y is —CN (TPC-9) attached at the para position;

where R is

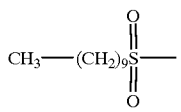

X is —H and Y is —CF₃ (TMF-10) or —CN (TMC-10) attached at the meta position;
where R is

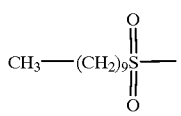

X is —H and Y is —CN (TPC-10) attached at the para position;
where R is

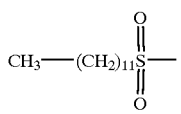

X is —H and Y is —CF₃ (TMF-12) attached at the meta position;
where R is

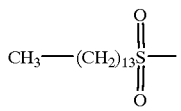

X is —H and Y is —CF₃ (TMF-14) attached at the meta position.

The compounds of this invention are synthesized by reacting a salicylic acid with a chlorosulfonic acid to form a 5-chlorosulfonylsalicylic acid. The 5-chlorosulfonylsalicylic acid is then reacted with an alkali metal sulfite to form 5-sulfinylsalicylic acid which is then reacted with an appropriate alkyl halide to produce the 5-alkylsulfonylsalicylic acid. More specifically the compounds of this invention can be synthesized according to the method disclosed in U.S. Pat. No. 4,939,132 which method is hereby incorporated by reference.

An advantage of the compounds of the present invention is that they have unexpectedly higher potency than the anti-inflammatory salicylanilide derivatives disclosed previously (Ritchey, U.S. Pat. No. 4,742,083). In the compounds of the present invention, the 5-alkyl groups are connected to the salicylanilides via a sulfonyl group whereas, in the compounds disclosed in U.S. Pat. No. 4,742,083, the 5-alkyl or 5-acyl groups are connected to the salicylanilides either directly or through

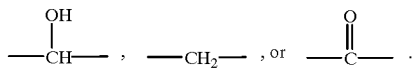

The introduction of the sulfonyl group at the 5- position surprisingly confers a significantly higher potency to the compounds of the present invention.

Since these compounds are highly lipophilic, they are insoluble in H₂O. However, and quite unexpectedly, these compounds were found to be soluble in aqueous solutions of both anionic and non-ionic detergents at concentrations routinely used in topical applications. This property of these compounds makes them suitable for topical formulations with a low risk of systemic uptake because of their high lipophilicity. Suitable detergents include but are not limited to non-ionic detergent Tween 80™ and anionic detergent sodium lauryl sulfate (SLS). In a preferred embodiment, the compounds of the present invention are dissolved in 0.5% to 4% Tween 80™ or SLS. In a more preferred embodiment, the compounds are dissolved in 2% SLS.

The compounds of this invention may be incorporated into formulations for topical application by methods well known to those skilled in the art. The compounds may be incorporated in a pharmaceutically acceptable carrier containing nonionic or anionic detergents. The formulation may include other surfactants. Suitable carrier bases include but are not limited to petroleum jelly, lanolin, paraffin wax, alkanols and mixtures thereof. By using a base such as lanolin or petroleum jelly, a spreadable formulation is obtained and by using a base such as paraffin wax, a stick for topical application is obtained. In addition, the compounds of this invention may also be incorporated into liquid carriers containing non-ionic or anionic detergents. In a preferred embodiment, the final concentration of the 5-alkylsulfonylsalicylanilide compound in between about 0.1% to about 1.0%. In a more preferred embodiment, the final concentration of the compound is between about 0.1% to about 0.3%.

The method in accordance with the present invention comprises contacting the inflamed area with the compounds of this invention. Applications include, but are not limited to, topical formulations for mouth, skin, scalp, ear, nose, eyes, vagina and rectum. Thus, these compounds can be used, without limitation, in tooth pastes, mouth rinses, soaps, shampoos, skin ointments, skin lotions, eye ointments, eye drops, ear drops, and nasal drops. In addition, the compositions of the present invention can be incorporated in protective topical coverings, including but not limited to, pads, bandages, dressings and plasters. Inflammatory conditions treated by these compounds includes various disorders like gingivitis, acne, arthritis, rosacea, eye inflammation including conjunctivitis, and inflammatory bowel diseases including Crohn's disease.

The compounds of this invention may also be used in topical formulations for veterinary use for the relief of inflammation in various conditions including gingivitis, conjunctivitis and arthritis. The formulations can be applied to, without limitation, mouth, skin, scalp, ear, nose, eyes, vagina and rectum.

The following examples illustrate the invention.

EXAMPLE 1

The solubility of representative compounds of this invention in various solvent systems was determined. The solvents included ethanol, propylene glycol, SLS, Tween 80™ and combinations thereof.

| Solvent System | Salifluor | TPC-10 | TMC-10 | TMF-10 | TMF-12 |
|---|---|---|---|---|---|
| Ethanol @ 19° C. | 13.04 | 11.5 | 36.7 | 44.67 | 13.59 ($22°$ C.) |
| Propylene Glycol @ 20° C. | 0.55 | 0.81 | 1.94 | 1.7 | 6.66 |
| pH 10 K-buffer @ 35° C. | $1.14 \times 10^{-3}$ | $3.45 \times 10^{-3}$ | $5.58 \times 10^{-3}$ | $<1 \times 10^{-4}$ | — |
| pH 10 Na-buffer @ 22° C. | $3.91 \times 10^{-3}$ | $9.16 \times 10^{-3}$ | $7.21 \times 10^{-3}$ | $1.89 \times 10^{-3}$ | $<1 \times 10^{-4}$ |
| +0.5% SLS | — | 0.3 | 3.13 | 0.37 | 1.28 |
| +1% SLS | 0.23 | 0.69 | 4.27 | 0.92 | 1.66 |
| +2% SLS | 0.29 | 0.91 | 6.68 | 1.28 | 2.93 |
| +4% SLS | 0.38 | 1.81 | 7.9 | 2.08 | 5.74 |
| +0.5% Tween 80 ™ | — | — | 0.77 | 0.76 | 1.34 |
| +1.5% Tween 80 ™ | — | — | 2.24 | 2.02 | 4.29 |
| +3.0% Tween 80 ™ | — | — | 4.69 | 4.13 | 8.34 |
| +2% SLS + 0.5% Tween 80 ™ | — | — | 3.98 | 1.35 | 3.54 |
| +2% SLS + 1.0% Tween 80 ™ | — | — | 4.74 | 1.91 | 4.01 |
| +2% SLS + 2.0% Tween 80 ™ | — | — | 5.05 | 2.87 | 5.86 |

The data exemplify a number of conclusions regarding the effect of structural variation on the physical properties of these agents. Although soluble to the extent of 1–4% in ethanol, they are insoluble in water unless ionized. The $pK_a$ of these compounds is about 5.2. As anions they have limited aqueous solubility, 0.0001–0.001% with slightly better solubility as sodium salts.

However, both anionic detergents e.g., SLS and non-ionic detergents e.g., Tween 80™ increase aqueous solubility to the 0.1%–0.8% range. Thus, even though the compounds of this invention are highly lipophilic, surprisingly, a 2% SLS solution can solubilize these hydrophobic compounds to useful concentration of 0.1% to 0.3% without the presence of any organic co-solvent, possibly due to more efficient micellar incorporation. The most potent compound of this invention, TMF-12, is more lipophilic than AMCF3-8 of U.S. Pat. No. 4,742,083, and at the same time displays a greater solubility than AMCF3-8 in the anionic and nonionic detergent solutions. As will be clear from Example 4 of this invention, TMF-12 is also more potent than AMCF3-8. As a result, even the most active compounds of this invention can be formulated at useful concentrations in simple systems compatible with mammalian usage including human usage. The detergent useful for solubilizing the compounds of this invention are routine additives in many topical formulation like tooth pastes and mouth rinses.

EXAMPLE 2

An analytical method to determine concentration and stability of some representative compounds of this invention in solution employing high pressure liquid chromatography (HPLC) was developed and validated. Both isocratic and gradient mobile phases of acetonitrile, water and methanol were investigated on a C-18 silica reverse solid phase column (Zorbax). Results were obtained using a 12 minute gradient of 80% to 100% methanol/water at a flow rate of 1.5 ml/minutes. Detection was carried out by measuring absorbance at 280 nm. Under these conditions TMF-10 and TMC-10 each produced symmetrical peaks with retention times of 7.5 and 3.0 minutes, respectively. TMF-8 and TMF-12 had retention times of 4 and 9 minutes respectively. Each compound had a linear relationship between concentration injected and area under the curve with correlation coefficients no less than 0.99. The lowest detectable quantity measured for all three compounds was 5.0 ng.

EXAMPLE 3

A 0.3 mg/ml solution of TMF-10 in 30% ethanolic water was maintained at 40° C. for several weeks. At various times samples were analyzed for decomposition employing the HPLC method described in Example 2. Following four weeks under these conditions, no decomposition of TMF-10 was detected.

EXAMPLE 4

The anti-inflammatory effect of selected compounds of this invention were compared to those of Triclosan™ and hydrocortisone in a modified 12-tetradecanoyl 13-phorbol acetate (TPA) mouse ear inflammation assay. TPA was used as an inflammogen rather than croton oil because TPA gives a well characterized inflammatory response at very low concentrations. The use of this mouse model has been shown to reflect the clinical parameters characteristic of inflammatory responses in humans and predictive of the effectiveness of therapeutic agents in patients (see for example, Kimura et al., 1995, *Biological and Pharmaceutical Bull.* 18:1617–1619; Rao et al., 1994, *J. Lipid Mediators & Cell Signaling* 10:213–228; Fretland et al., 1995, *Inflammation* 19:333–346). This model can therefore be used to study the pharmacokinetics, clinical efficacy and adverse side effects of anti-inflammatory agents. To quantitate inflammation, ear punches from treated animals were used to measure increased ear mass (edema) and myeloperoxidase (MPO) activity. For the inhibition studies, ear biopsies were weighed six hours after treatment with TPA and the simultaneous application of the compound of the present invention. All the compounds were diluted in acetone. Following this, the biopsies were frozen and subsequently used to measure inhibition of MPO activity which is an estimate of polymorphonuclear (PMN) lymphocyte activity in the affected area. Percent inhibition of edema was calculated as $[c-t]/c \times 100$, where c and t are increases in ear weight in control and treated mice, respectively.

Initially a dose-response curve for TPA-induced mouse ear edema was generated in order to determine the concentration of TPA to be employed in the inhibition studies. TPA produced a theoretical dose-response curve for edema with an $ED_{50}$ of 80 ng/ear and an $ED_{90}$ of 200 ng/ear in two separate experiments. $ED_{50}$ is the dose at which 50% of the maximum effect was observed while $ED_{90}$ is the dose at which 90% of the maximum effect was observed. TMF-12, which is representative of all the compounds tested in this study, inhibited TPA induced mouse ear edema in a dose-dependent fashion. The $ED_{50}$ values for the compounds tested are as follows:

| Compound | $ED_{50}$ (μg/20 ul) | $ED_{90}$ (μg/20 ul) |
|---|---|---|
| TMF-8 | 36.1 | 273.2 |
| TMF-10 | 31.9 | 225.1 |
| TMF-12 | 15.3 | 121.6 |
| TPC-10 | 64.3 | 548.6 |
| TMC-10 | 72.6 | 615.5 |
| Salifluor | 155.9 | 1241.8 |
| Triclosan ™ | 133.9 | 832.2 |

Each of the compounds of this invention was more potent than Salifluor (AMCF3-8), which is the most potent compound disclosed in U.S. Pat. No. 4,742,083. TMF-12 was the most potent of all, ten times more potent than Salifluor. The compounds of this invention are also more potent than Triclosan™. Hydrocortisone, a steroid, was the most potent anti-inflammatory agent tested.

EXAMPLE 5

As a confirmation of the anti-inflammatory activity and in an attempt to further define the mechanism of inhibition produced by the alkylsulfonylsalicylanilides, MPO activity was measured in representative ear biopsies. The enzyme was extracted from the tissue by using a combination of homogenization in the presence of a detergent, freezing and thawing, and sonication. The change in absorbance was measured with time using o-dianisidine and $H_2O_2$ as the substrate in an automated plate reader. As shown below, TPA-induced increase in MPO was inhibited in TMF-12 treated ears at a dose approximately 10-fold less than that which inhibited edema.

| TMF-12 (μg/20 μl) | MPO Activity (Δ OD/min) |
|---|---|
| 0 | 624.9 |
| 0.8 | 590.2 |
| 1.24 | 327.3 |
| 8 | 56.5 |
| 12.4 | 54.8 |
| 80 | 27.6 |
| 124 | 21 |

While not intending to be bound by any particular theory, these results suggest that one of the mechanisms through which the alkylsulfonylsalicylanilides inhibit inflammation is via inhibition of the PMN pathway, preventing macrophage infiltration and release of autacoids such as histamine, nitric oxide, arachidonic acid and peroxides.

EXAMPLE 6

To test for tolerance of the administered compounds, male weaning Sprague-Dawley rats were fed in a single dose of 2.5 or 0.75 g/kg of TMF-12, TMF-10, TMC-10 or TPC-10 in 5% carboxymethyl cellulose (CMC) or CMC alone. The animals (6–7 rats per group) were observed for 7 days for morbidity or mortality. At completion of the 7 day observation period, necropsies were performed on all animals. No statistical weight differences were noted between the control group (sham treated) and the experimental drug treated groups, indicating that there was no loss of appetite due to the drug. All animals doubled their weight during the seven day experimental period. No illness or deaths occurred during the seven day period. No observable gross pathology attributable to the drugs was seen at necropsy.

It is appreciated that various modifications to the inventive concepts described herein may be apparent to those skilled in the art without departing from the spirit and scope of the present invention defined by the hereinafter appended claims.

What is claimed is:

1. A method of treating inflammation in a mammal, which comprises contacting the affected area with an amount sufficient to ameliorate the inflammatory condition, of a compound of the following formula

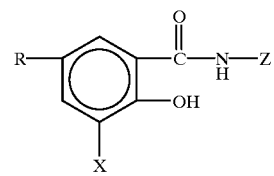

in a pharmaceutically acceptable carrier, said carrier comprising a detergent, wherein Z is a substituted phenyl ring, wherein the substitution on Z is selected from the group consisting of —$CF_3$, —CN and —$NO_2$, wherein R is an alkylsulfonyl group of 1 to 20 carbon atoms, and X is selected from the group consisting of —CN, —$NO_2$, —H, halogen, lower alkyl and lower haloalkyl.

2. The method of claim 1, wherein said compound has a partition coefficient greater than 4 and the substituted moieties in the phenyl ring Z group have a combined overall electron withdrawing effect on the phenyl ring of the Z group.

3. The method of claim 1, wherein the compound is

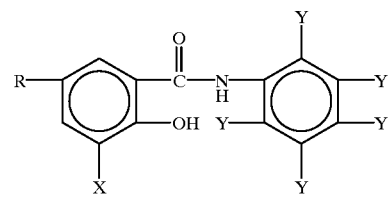

and Y is independently at each occurrence an electron withdrawing group.

4. The method of claim 3, wherein Y is selected from the group consisting of —$CF_3$, —CN and —$NO_2$.

5. The method of claim 1, wherein the compound has the formula

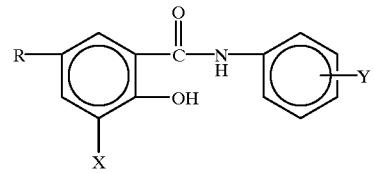

X is —H and Y is selected from the group consisting of —$CF_3$ and —CN.

6. The method of claim 5, wherein R is

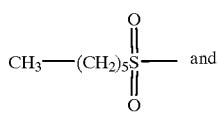 and and
Y is —CF₃ attached at the meta position.

7. The method of claim 5, wherein R is

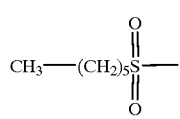

and Y is —CN attached at the meta position.

8. The method of claim 5, wherein R is

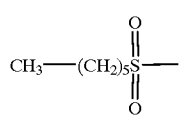

and Y is —CN attached at the para position.

9. The method of claim 5, wherein R is

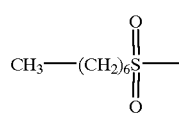

and Y is —CF₃ attached at the meta position.

10. The method of claim 5, wherein R is

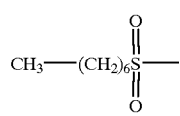

and Y is —CN attached at the meta position.

11. The method of claim 5, wherein R is

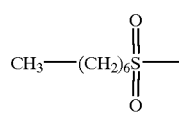

and Y is —CN attached at the para position.

12. The method of claim 5, wherein R is

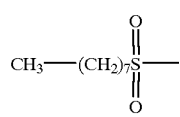

and Y is —CF₃ attached at the meta position.

13. The method of claim 5, wherein R is

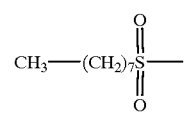

and Y is —CN attached at the meta position.

14. The method of claim 5, wherein R is

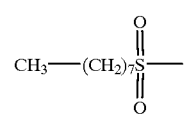

and Y is —CN attached at the para position.

15. The method of claim 5, wherein R is

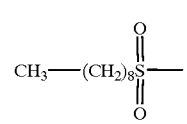

and Y is —CF₃ attached at the meta position.

16. The method of claim 5, wherein R is

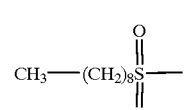

and Y is —CN attached at the meta position.

17. The method of claim 5, wherein R is

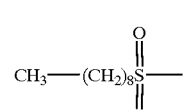

and Y is —CN attached at the para position.

18. The method of claim 5, wherein R is

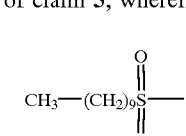

and Y is —CF₃ attached at the meta position.

19. The method of claim 5, wherein R is

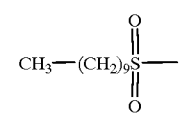

and Y is —CN attached at the meta position.

20. The method of claim 5, wherein R is

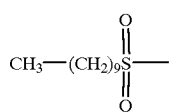

and Y is —CN attached at the para position.

21. The method of claim 5, wherein R is

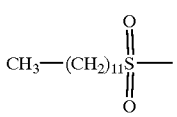

and Y is —CF$_3$ attached at the meta position.

22. The method of claim 5, wherein R is

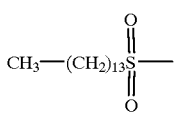

and Y is 13 CF$_3$ attached at the meta position.

23. The method of claim 1, wherein the pharmaceutically acceptable carrier comprises a material selected from the group consisting of petroleum jelly, lanolin, paraffin wax, alkanols and mixtures thereof.

24. The method of claim 1, wherein the pharmaceutically acceptable carrier is a liquid.

25. The method of claim 1, wherein said detergent is selected from the group consisting of non-ionic detergent, anionic detergent and mixtures thereof.

26. The method of claim 25, wherein the non ionic detergent is Tween-80™.

27. The method of claim 26, wherein the concentration of Tween 80™ in the pharmaceutically acceptable carrier is from about 0.5 percent to about 3 percent.

28. The method of claim 25, wherein the anionic detergent is sodium lauryl sulfate.

29. The method of claim 28, wherein the concentration of sodium lauryl sulfate is from about 0.5 percent to about 4 percent.

30. The method of claim 25, wherein the concentration of the compound in the pharmaceutically acceptable carrier is between about 0.1% to about 1.0%.

31. The method of claim 30, wherein the concentration of the compound in the pharmaceutically acceptable carrier is between about 0.1% to about 0.3%.

32. The method of claim 1, wherein the mammal is a human being.

33. The method of claim 1, wherein the mammal is an animal.

* * * * *